(12) United States Patent
Noda (10) Patent No.: US 7,135,150 B2
(45) Date of Patent: Nov. 14, 2006

(54) BLOOD EXAMINATION INSTRUMENT (75) Inventor: Yuichiro Noda, Kyoto (JP)

(73) Assignee: Arkray, Inc., Kyoto (JP)

( * ) Notice: Subject to any disclaimer, the term of this patent is extended or adjusted under 35 U.S.C. 154(b) by 69 days.

(21) Appl. No.: 10/476,404

(22) PCT Filed: Sep. 2, 2002

(86) PCT No.: PCT/JP02/08857

§ 371 (c)(1),
(2), (4) Date: Oct. 28, 2003

(87) PCT Pub. No.: WO03/021255

PCT Pub. Date: Mar. 13, 2003

(65) Prior Publication Data
US 2004/0170535 A1 Sep. 2, 2004

(30) Foreign Application Priority Data
Sep. 3, 2001 (JP) ............................. 2001-266173

(51) Int. Cl.
B01L 11/00 (2006.01)

(52) U.S. Cl. .................... 422/101; 422/99; 422/100; 436/180; 210/500.1

(58) Field of Classification Search .......... 422/99–101; 210/650, 500.1; 436/180
See application file for complete search history.

(56) References Cited

U.S. PATENT DOCUMENTS

| 5,423,989 A | * | 6/1995 | Allen et al. .................. 210/650 |
| 5,558,834 A | | 9/1996 | Chu et al. |
| 5,590,383 A | * | 12/1996 | Sekhar et al. .................. 419/2 |
| 2001/0005488 A1 | | 6/2001 | Hirao et al. |

FOREIGN PATENT DOCUMENTS

| JP | 5-209877 | 8/1993 |
| JP | 2001-165930 | 6/2001 |
| JP | 2001-188066 | 7/2001 |

* cited by examiner

Primary Examiner—Jill Warden
Assistant Examiner—Jyoti Nagpaul
(74) Attorney, Agent, or Firm—Hamre, Schumann, Mueller & Larson, P.C.

(57) ABSTRACT

A blood testing tool is provided, which can recover blood plasma or blood serum with a high yield without causing hemolysis of blood cells. A recovery porous membrane 1 to be impregnated with blood serum or blood plasma contained in blood and retain it and a separation porous membrane 2 for separating blood cells from the blood are provided. The separation porous membrane 2 is laminated on the recovery porous membrane 1 while satisfying the condition that pores on an upper surface side of the recovery porous membrane have an average pore size that is in a range from 10 to 1000 μm and is larger than that of pores on a lower surface side of the separation porous membrane, thus providing a blood testing tool according to the present invention.

9 Claims, 4 Drawing Sheets

BLOOD EXAMINATION INSTRUMENT

TECHNICAL FIELD

The present invention relates to a blood testing tool used for a blood test.

BACKGROUND ART

In a blood test, a blood testing tool having a porous material to be impregnated with blood conventionally has been used for various purposes.

According to such a blood testing tool, the test can be carried out, for example, by impregnating the porous material with blood so that a component in the blood reacts with a reagent that has been provided in the porous material beforehand and then measuring the result directly by an optical or electrochemical method. Alternatively, the blood may be extracted from the porous material and recovered, and the test may be carried out on this as a sample.

Such a blood testing tool has been used in general clinical tests or the like. In recent years, the suitability of such a blood testing tool has been studied for use in remote clinical testing systems. Indeed, it is actually used in certain remote clinical testing systems. In such a remote clinical testing system, a patient collects blood by himself at home, and the blood testing tool is impregnated with the blood. This then is dried, and the blood testing tool then is mailed to a test institute such as a hospital for testing. The system allows the patient who mailed the blood to be informed of the test result by mail or the like without visiting the hospital. In addition, because the patient can visit the hospital or the like for treatment after receiving the test result, the necessity of collecting blood at the hospital is eliminated, which reduces the labors of both the hospital stuff and the patient.

When the test item is a component contained in blood serum or blood plasma, such as blood glucose or the like, it is necessary to separate blood cells from blood in the blood testing tool. A conventional blood testing tool generally is a laminate in which a blood cell separator such as a glass filter or the like is laminated on a recovery porous material into which blood serum or blood plasma penetrates. In such a blood testing tool, when blood is supplied to the upper surface of the blood cell separator, the blood moves in the thickness direction inside the blood cell separator, during which blood cells in the blood are retained in the blood cell separator so that only blood serum or blood plasma passes through the blood cell separator. The blood serum or blood plasma having passed through the blood cell separator penetrates into the recovery porous material as the lower layer of the laminate and is retained therein (hereinafter, such blood cell separation is referred to as "vertical separation"). In such vertical separation, a surface area involved in the separation is greater than in transverse separation to be described later. Thus, the blood serum or blood plasma having passed through the separator penetrates, thereby allowing an excellent recovery rate to be achieved.

However, a laminate-type blood testing tool employing such vertical separation has a problem in that the blood cells retained in the blood cell separator may hemolyze at the interface between the blood cell separator and the recovery porous material. If such hemolysis occurs, components that flowed out from the blood cells due to the hemolysis penetrate into the recovery porous material as the lower layer of the laminate and interfere with the measurement.

In order to solve the problem caused in the vertical separation, a blood testing tool has been developed in which blood moves in a direction parallel to the surface (which is a transverse direction and hereinafter, referred to simply as a "surface direction") rather than in a thickness direction (a vertical direction) to separate blood cells (hereinafter, such blood cell separation is referred to as "transverse separation", which is disclosed in JP 2001-188066 A etc.). The transverse separation can be carried out, for example, in a blood testing tool including an asymmetric porous membrane with pores whose sizes vary in the surface direction. For example, when blood is supplied to the asymmetric porous membrane from the side having larger pores, the blood moves from the upstream with larger pores to the downstream with smaller pores along the surface direction by the capillary phenomenon. When the blood cells reach the portion with pores through which they cannot pass, they are retained therein so that only blood serum or blood plasma penetrates further downstream. Thus, in this blood testing tool, since blood cells are separated during the movement in the surface direction due to the variation in pore sizes, the above-described problem of the hemolysis of blood cells at the interface is not caused. Therefore, it is possible to recover only blood serum or blood plasma containing no components of blood cells.

DISCLOSURE OF INVENTION

However, in a blood testing tool employing such transverse separation, since blood moves in the surface direction as opposed to the vertical separation in which blood penetrates in the thickness direction, a contact surface between a separation portion and a recovery portion is small, which makes it difficult for blood serum or blood plasma to penetrate into the recovery portion. This lowers the recovery rate of blood serum or blood plasma. Therefore, in the case of the transverse separation, it is necessary to supply a larger amount of blood than that required in the vertical separation to recover a sufficient amount of sample, such as blood serum or the like, for carrying out a test. Furthermore, particularly in the case of the remote clinical testing system where a patient collects blood himself, an increase in an amount of blood plasma or blood serum recovered from blood has been demanded because there is the difficulty of obtaining a large amount of blood and there are many test items.

Therefore, it is an object of the present invention to provide a blood testing tool that can separate blood cells easily without causing hemolysis and can recover blood plasma or blood serum with a high yield.

In order to achieve the above-described object, a blood testing tool according to the present invention includes: a separation porous membrane for separating blood cells from blood; and a recovery porous membrane to be impregnated with and retain blood serum or blood plasma of the blood. The separation porous membrane is laminated on the recovery porous membrane. Pores on an upper surface side of the recovery porous membrane have an average pore size that is in a range from 10 to 1000 µm and is larger than that of pores on a lower surface side of the separation porous membrane.

Although the blood testing tool according to the present invention employs the above-described vertical separation, the blood cells that have been separated and retained in the separation porous membrane can be prevented from hemolyzing, unlike the case of the conventional blood testing tools. Thus, the blood serum or blood plasma having passed through the separation porous membrane to penetrate into the recovery porous membrane contains no components of the blood cells. Therefore, components in the blood plasma or blood serum can be measured with high accuracy. Furthermore, since the hemolysis is prevented as described above, it also becomes possible to subject the recovery porous membrane, from which the separation porous membrane has been peeled off and removed, to measurement directly according to an optical method, visual observation, or the like. In addition, since the blood testing tool employs vertical separation, blood serum or blood plasma can be obtained with a high recovery rate. Moreover, when the pore size of the pores in the separation porous membrane and the pore size of the pores in the recovery porous membrane are set so as to satisfy the above-described relationship, these porous membranes can be prevented from adhering to each other and separated easily even after blood serum or blood plasma penetrates into the recovery porous membrane and then is dried. Furthermore, in the blood testing tool according to the present invention, the hemolysis can be prevented sufficiently regardless of the operation time because of its structure. This eliminates the necessity of, for example, performing blood cell separation quickly, performing the measurement or collecting blood plasma or the like immediately after the blood cell separation, or the like, to prevent hemolysis from occurring. Thus, even the patient or the like can collect blood plasma easily without controlling the operation time. In addition, the blood testing tool dried after blood plasma has penetrated into the recovery porous membrane can be, for example, stored or mailed in a stable condition. As described above, the blood testing tool according to the present invention can solve all the problems regarding the hemolysis, recovery rate, ease of operation, etc., which exist in the conventional blood testing tools employing vertical separation and transverse separation. Thus, the blood testing tool according to the present invention is useful particularly in the above-described remote clinical testing system.

In the blood testing tool according to the present invention, it is preferable that the pores on the lower surface side of the separation porous membrane have an average pore size that does not allow the blood cells to pass. In the present invention, the "pores with a size that does not allow blood cells to pass" are not limited to the pores with a smaller size than spherical diameters of blood cells, but may be pores through which blood cells eventually cannot pass regardless of the mechanism of preventing blood cells from passing through the pores. Therefore, the pores with a size that does not allow blood cells to pass may include pores larger than the spherical diameters of blood cells.

In the blood testing tool according to the present invention, it is preferable that the pores on the upper surface side of the recovery porous membrane have an average pore size that is 10 to 100 times larger than that of the pores on the lower surface side of the separation porous membrane.

In the blood testing tool according to the present invention, the pores on the lower surface side of the separation porous membrane have an average pore size in a range from 1.0 to 10 µm.

In the blood testing tool according to the present invention, it is preferable that the separation porous membrane is an asymmetric porous membrane with a pore size distribution in which an average pore size varies so that it is reduced continuously or discontinuously in a thickness direction. In such an asymmetric porous membrane, a pore size varies in a thickness direction. Thus, as blood moves in the thickness direction inside the separation porous membrane, fewer and fewer blood cells can pass through the pores, and the blood cells are retained when they reach the portion with pores through which the blood cells cannot pass. Therefore, the clogging hardly occurs in this blood testing tool and blood cells can be separated easily and quickly. In the present invention, the "average pore size varies so that it is reduced discontinuously" means that the average pore size may vary, for example, to be reduced in a stepwise manner.

Furthermore, in the blood testing tool according to the present invention, it is preferable that the recovery porous membrane is an asymmetric porous membrane with a pore size distribution in which an average pore size varies so that it is reduced continuously or discontinuously in a thickness direction. If the recovery porous membrane is the asymmetric porous membrane, a pore size reduces in the thickness direction while the pore size of the pores on the upper surface side satisfies the above-described condition. Thus, the porosity of the recovery porous membrane can be decreased. Therefore, the recovery porous membrane can have an excellent strength because of its structure, thus allowing excellent handling.

In the blood testing tool according to the present invention, it is preferable that the maximum pore size of the pores in the separation porous membrane is in a range from 10 to 1000 µm and the minimum pore size of the same is in a range from 1.0 to 10 µm.

In the blood testing tool according to the present invention, it is preferable that the maximum pore size of the pores in the recovery porous membrane is in a range from 10 to 1000 µm and the minimum pore size of the same is in a range from 1.0 to 10 µm.

In the blood testing tool according to the present invention, in addition to the asymmetrical porous membrane as described above, a symmetric porous membrane or the like, for example, may be used as the recovery porous membrane or the separation porous membrane.

In the blood testing tool according to the present invention, it is preferable that the recovery porous membrane is supported by a supporter. Accordingly, regardless of the strength of the recovery porous membrane, a blood testing tool with a sufficient strength can be obtained, which enables easy handling.

In the blood testing tool according to the present invention, the porous membranes preferably are formed using a resin selected from polysulfone, polyethersulfone, polyamide, polyimide, polycarbonate, polystyrene, polyaryl hydrazide, nitrocellulose, polyvinyldifluoride, cellulose acetate, polyethylene, and the like. Among these, polyethersulfone is more preferable.

BRIEF DESCRIPTION OF DRAWINGS

FIGS. 1A and 1B show a blood testing tool according to one example of the present invention, wherein

FIGS. 2A and 2B show a blood testing tool according to another example of the present invention, wherein

FIGS. 4A and 4B show a blood testing tool according to a comparative example, wherein

BEST MODE FOR CARRYING OUT THE INVENTION (Embodiment 1)

Figure 1:
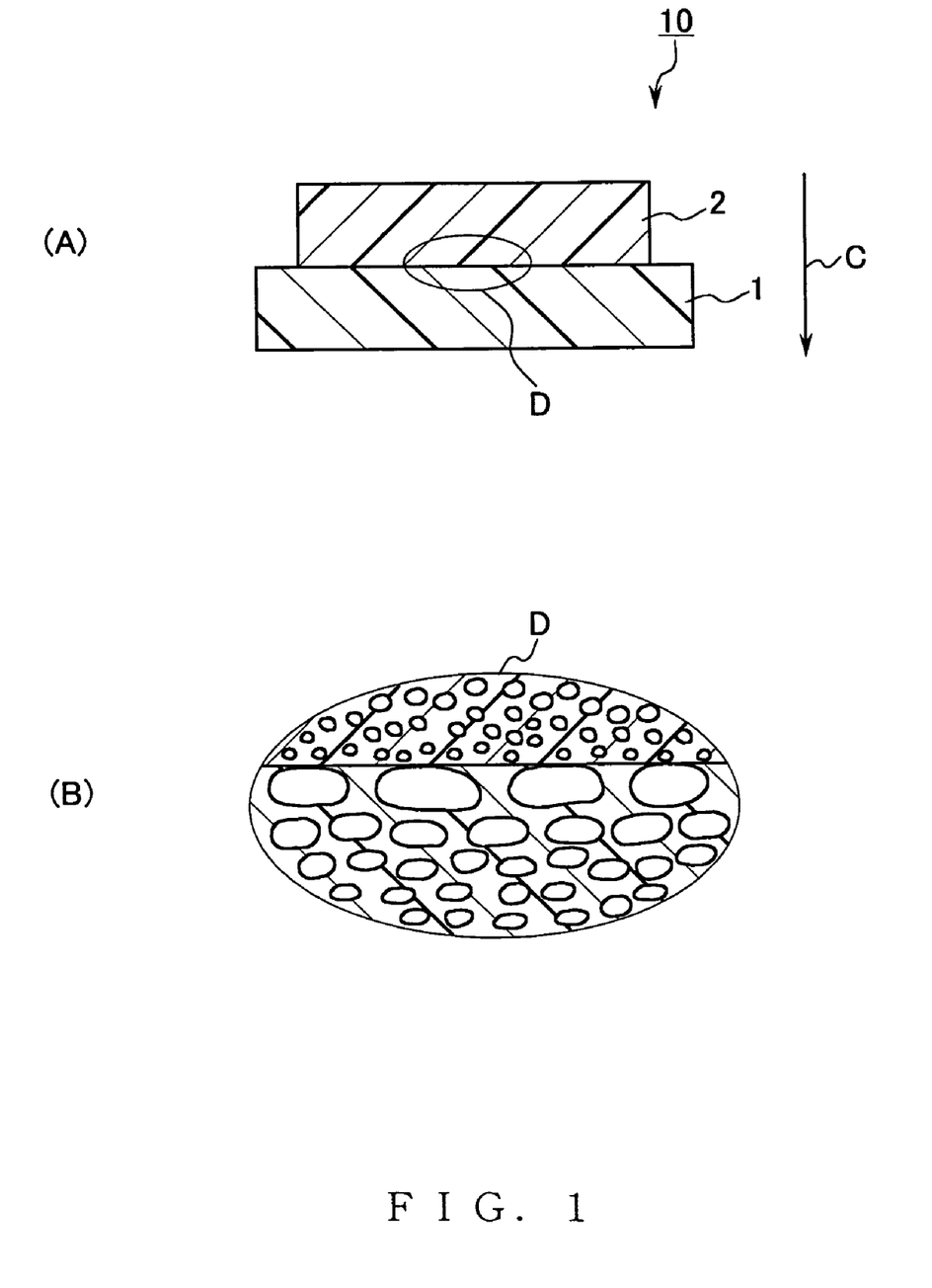
FIG. 1A is a cross-sectional view and FIG. 1B is an enlarged view of a portion of FIG. 1A.

FIGS. 1A and 1B show a blood testing tool according to one example of the present invention. FIG. 1A is a cross-sectional view of the blood testing tool. As shown in FIG. 1A, this blood testing tool 10 includes a recovery porous membrane 1 and a separation porous membrane 2 laminated on this recovery porous membrane 1. Both the porous membranes 1 and 2 have a pore size distribution in which an average pore size varies so that it is reduced continuously in the thickness direction (the direction indicated with the arrow C in FIG. 1A). As shown in FIG. 1B, which is an enlarged view of the portion D in FIG. 1A, pores on the upper surface side of the recovery porous membrane 1 are larger than those on the lower surface side of the separation porous membrane.

In the recovery porous membrane 1, the maximum pore size of the pores on the upper surface side is, for example, in the range from 10 to 1000 μm, preferably 15 to 50 μm, and more preferably 25 to 50 μm, and the minimum pore size of the pores on the lower surface side is, for example, in the range from 1 to 10 μm, preferably 1.5 to 3.0 μm, and more preferably 2.0 to 2.5 μm. On the other hand, in the separation porous membrane 2, the maximum pore size of the pores on the upper surface side is, for example, in the range from 10 to 1000 μm, preferably 15 to 50 μm, and more preferably 25 to 50 μm, and the minimum pore size on the lower surface side is, for example, in the range from 1 to 10 μm, preferably 1.5 to 3.0 μm, and more preferably 2.0 to 2.5 μm.

The relationship between the pore size of the pores in the recovery porous membrane 1 and the pore size of the pores in the separation porous membrane 2 may be such that the pores on the upper surface side of the recovery porous membrane 1 have a pore size that is in a range from 10 to 1000 μm and is larger than that of the pores on the lower surface side of the separation porous membrane 2, as described above. The pores on the upper surface side of the recovery porous membrane 1 may have a pore size that is, for example, 10 to 100 times, preferably 10 to 30 times, and more preferably 10 to 20 times larger than that of the pores on the lower surface side of the separation porous membrane 2. Specifically, it is preferable that the pores on the upper surface side of the recovery porous membrane 1 have a pore size in the range from 10 to 1000 μm while the pores on the lower surface side of the separation porous membrane 2 have a pore size in the range from 1 to 10 μm. More preferably, the pores on the upper surface side of the recovery porous membrane 1 have a pore size in the range from 15 to 50 μum while the pores on the lower surface side of the separation porous membrane 2 have a pore size in the range from 1.5 to 3.0 μm. Particularly preferably, the pores on the upper surface side of the recovery porous membrane 1 have a pore size in the range from 25 to 50 μm while the pores on the lower surface side of the separation porous membrane 2 have a pore size in the range from 2.0 to 2.5 μm.

The size of the blood testing tool 10 is not particularly limited and can be determined as appropriate according to the amount of a blood specimen to be supplied or the like. When the whole blood to be supplied is about 80 to 120 μl, the size of the recovery porous membrane 1 preferably is 100 to 1000 μm for the thickness, 1 to 200 mm for the length, and 1 to 200 mm for the width; more preferably 150 to 500 μm for the thickness, 5 to 50 mm for the length, and 5 to 50 mm for the width; and still more preferably 200 to 400 μm for the thickness, 10 to 20 mm for the length, and 10 to 20 mm for the width. On the other hand, the size of the separation porous membrane 2 preferably is 100 to 1000 μm for the thickness, 1 to 500 mm for the length, and 1 to 500 mm for the width; more preferably 150 to 500 μm for the thickness, 5 to 100 mm for the length, and 5 to 100 mm for the width; and still more preferably 200 to 400 μm for the thickness, 10 to 50 mm for the length, and 10 to 50 mm for the width.

Asymmetric porous membranes to be used as the recovery porous membrane 1 and the separation porous membrane 2 preferably are formed using such resins as described above. Among these resins, polysulfone is preferable due to its ease of manufacture, its stiffness, and the like. Such asymmetric porous membranes may be produced using the above-described resins. Alternatively, commercially available asymmetric porous membranes, for example, polysulfone porous membranes manufactured by U.S. Filter Corporation, polyethersulfone porous membranes manufactured by Spectral Diagnostics Inc., and the like may be used.

The asymmetric porous membranes may be treated so as to be provided with hydrophilicity by being immersed in a treatment solution such as, for example, hydrophilic polymers such as hydroxypropylcellulose (HPC), polyvinyl alcohol (PVA), carboxymethylcellulose (CMC), or the like, amino acids such as glycine, lysine, or the like, lecithin, surfactants, or the like. This treatment can improve the blood penetration, thereby allowing blood to penetrate quickly. The concentration of the treatment solution is, for example, in the range from 1 to 50 wt %, and the time for an immersing process is, for example, in the range from 0.01 to 1 hour. As a solvent of the solution, for example, water, various organic solvents, or the like can be used. Examples of the organic solvents include alcohols such as ethanol or the like. The hydrophilicity may be given not only by the treatment using the above-described treatment solution but also by a physical method such as, for example, a plasma treatment, glow discharge, corona discharge, and ultraviolet irradiation.

In order to maintain the stability of components in blood plasma or blood serum to be retained, the recovery porous membrane 1 may contain a stabilizing agent, for example, saccharides such as sucrose, trehalose, lactose, glucose, or the like, salts such as sodium chloride, potassium chloride, or the like, buffers such as glycine, a phosphate buffer, a citrate buffer, or a Good's buffer, or the like. The content of the stabilizing agent can be determined as appropriate according to its kind or the like, but is, for instance, in the range from 0.01 to 100 mg per cubic centimeter of the porous membrane. One kind of stabilizing agent may be used, or two or more kinds may be used in combination.

In the production of the blood testing tool according to the present invention, the separation porous membrane may be laminated on the recovery porous membrane by, for example, merely placing it. Preferably, lamination of the separation porous membrane on the recovery porous membrane is carried out by, for example, performing the positioning of the separation porous membrane with respect to the recovery porous membrane and then pressing them together in a holder that will be described later, or by bonding or attaching by pressure the end portions of these porous membranes.

Next, an example of preparing a blood plasma sample or a blood serum sample by having the blood testing tool 10 become impregnated with and retain blood is described based on FIGS. 1A and 1B.

Initially, blood is dropped on the upper surface of the separation porous membrane 2. The blood dropped moves downwardly inside the separation porous membrane 2, during which blood cells in the blood reach the portion with pores through which they cannot pass and are captured. As a result, only blood plasma or blood serum passes through the separation porous membrane 2. The blood plasma or blood serum having passed through the separation porous membrane 2 penetrates further into the recovery porous membrane 1 as the lower layer of the laminate and is retained therein.

The blood testing tool 10 retaining the blood serum or blood plasma is dried by forced air drying, natural air drying, or the like. Thereafter, the separation porous membrane 2 is peeled off from the recovery porous membrane 1. As described above, in the blood testing tool according to the present invention, since the separation porous membrane 2 can be peeled off easily from the recovery porous membrane 1, there is no fear that the recovery porous membrane 1 might be broken or that the separation porous membrane 2 might be removed only partially so that some portions thereof remain in the recovery porous membrane 1. Accordingly, there is no fear that the recovery rate of blood serum or blood plasma might be decreased or that the blood serum or blood plasma recovered might contain components of blood cells.

Next, the recovery porous membrane 1 is put, for example, in a test tube and an extractant is added thereto, which then is left, thus extracting and recovering blood plasma or blood serum. The extractant is not particularly limited as long as it can extract blood plasma or blood serum and does not affect the detection of analytical target components in the blood plasma or blood serum. As the extractant, for example, a buffer solution, a physiological salt solution, purified water, a protein solution, or the like, or a mixture thereof may be used. Examples of the buffer solution include various buffer solutions including phosphoric acid, citric acid, hydrochloric acid, acetic acid, or the like, and the pH of the buffer solution is, for example, in the range from 6 to 8. The amount of the extractant to be added is not particularly limited and can be determined as appropriate according to the size of the recovery porous membrane or the like. The amount is, for example, 1 to 1000 times the volume of the recovery porous membrane. In addition, the time for an extracting process is not particularly limited and is, for example, in the range from 1 to 300 minutes.

Using the recovered solution, the analytical target components in the blood plasma or blood serum are measured, and the amounts of the components thus are determined.

Alternatively, it is also possible to analyze the blood plasma or blood serum retained in the recovery porous membrane 1 in this blood testing tool 10 without recovering it using the extractant. To this end, an analytical reagent may be provided in the recovery porous membrane 1 beforehand. Furthermore, in addition to the analytical reagent provided in the recovery porous membrane 1 as described above, a pretreatment reagent also may be provided in the separation porous membrane 2. Still further, reagents that are not allowed to be mixed with each other may be provided separately in the recovery porous membrane 1 and the separation porous membrane 2 so that these reagents react with each other when the blood plasma or the like penetrates through the porous membranes. Examples of the method for providing the reagent in these porous membranes include a printing method, an impregnation method, a spraying method, and the like.

The reagent is not limited and can be determined as appropriate according to the kind of an analytical target component. Examples of the components of the reagent include various enzymes, buffer materials such as phosphate, carbonate, and the like, color developing agents, and the like. Specifically, when the analytical target component is glucose, glucokinase, glucose-6-phosphate dehydrogenase, β-NADP, ATP, a buffer, and the like may be provided.

Furthermore, the reagent to be provided in the separation porous membrane 2 may be the above-described pretreatment reagent, such as an enzyme capable of removing beforehand a substance contained in a specimen that interferes with the measurement, a reagent for promoting the reaction, or the like. Specific examples of the pretreatment reagent include ascorbate oxidase and uricase, which remove ascorbic acid, uric acid, and the like having a strong reducing ability, surfactants for dissolving an aggregated specimen to improve the reaction efficiency, and the like. Examples of the combination of reagents that cannot be mixed with each other include those of two or more reagents that react with each other to cause color development or the like and thus should be held independently before a substance to be measured reacts with the reagents. Specific examples of such combinations include the combination of a tetrazolium salt as a color developing agent and an alkaline buffer. Although they must be present in combination during the reaction, if they contact with each other before the reaction, the tetrazolium salt develops color. Thus, in this case, the alkaline buffer may be provided in either one of the recovery porous membrane 1 and the separation porous membrane 2 and the tetrazolium salt may be provided in the other porous membrane.

In this blood testing tool 10, when blood is supplied to the testing tool and only blood serum or blood plasma penetrates into the recovery porous membrane 1 as described above, various analytical target components react with detection reagents, respectively, in the recovery porous membrane 1. Then, after the separation porous membrane 2 is peeled off and removed, the color development or the like caused by the reactions in the recovery porous membrane 1 may be detected directly by an electrochemical method or an optical method (including visual observation). Thus, the analysis can be conducted easily. Furthermore, the observation or the like of the recovery porous membrane 1 may be conducted from the lower surface side thereof without peeling off the separation porous membrane 2 from the recovery porous membrane 1.

The recovery porous membrane on which the separation porous membrane is laminated may be disposed on a supporter. Accordingly, the strength of the blood testing tool is improved, thereby enabling still easier handling.

As the material for forming the supporter, for example, plastic such as polystyrene, polyethylene terephthalate (PET), polyvinyl chloride, acrylic resins, acrylonitrile-butadiene-styrene copolymer (ABS), or the like can be used. The material is not limited to only one of them, and two or more of them may be used in combination.

When the blood testing tool 10 is subjected to measurement from the supporter side directly by the optical method or the like as described above, it is preferable that, for example, the supporter has optical transparency. In this case, for example, polystyrene, PET, acrylic resins, or the like is preferred as the material.

(Embodiment 2)

Figure 2:
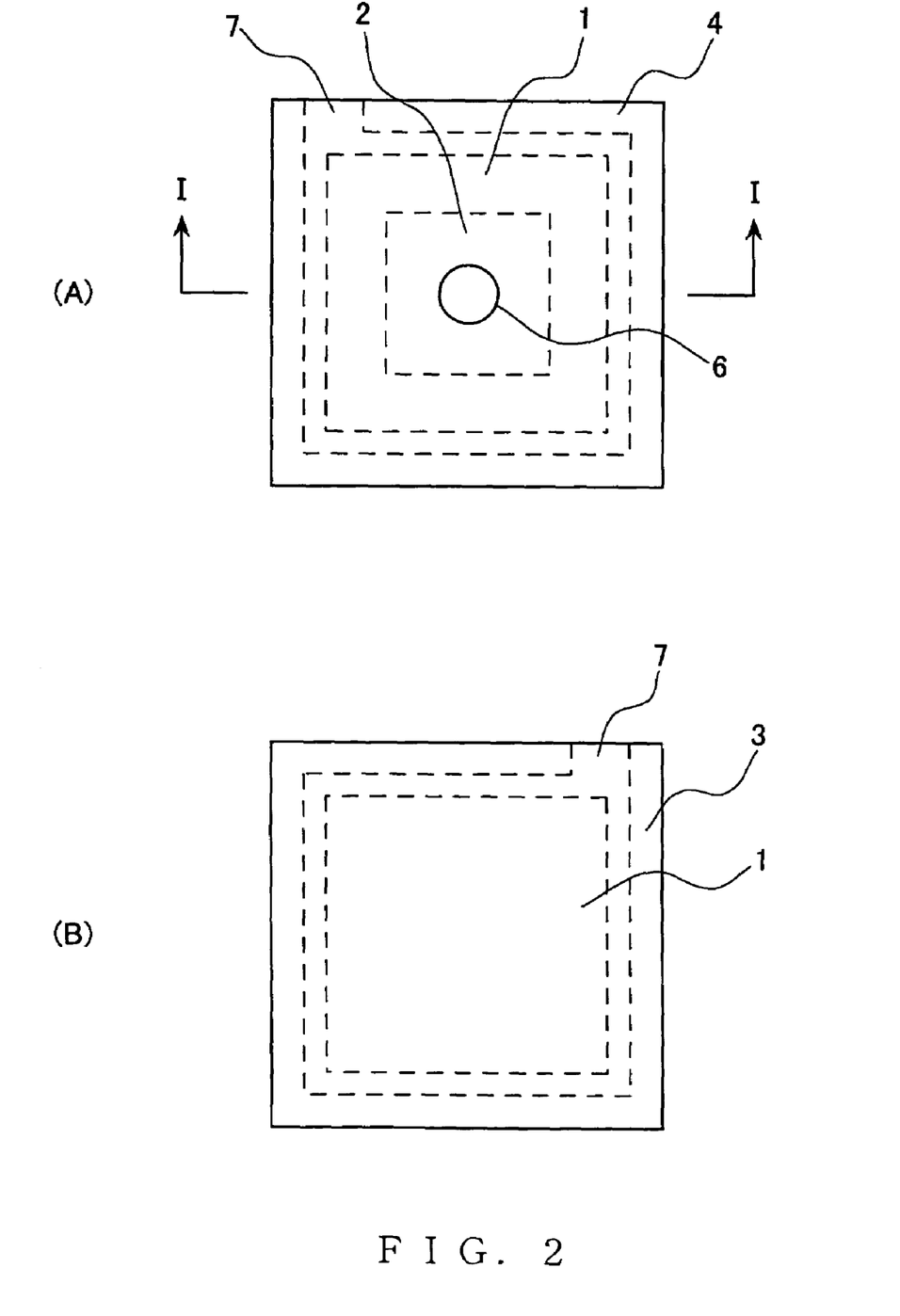
FIG. 2A is a plan view and FIG. 2B is a back face view.
Figure 3:
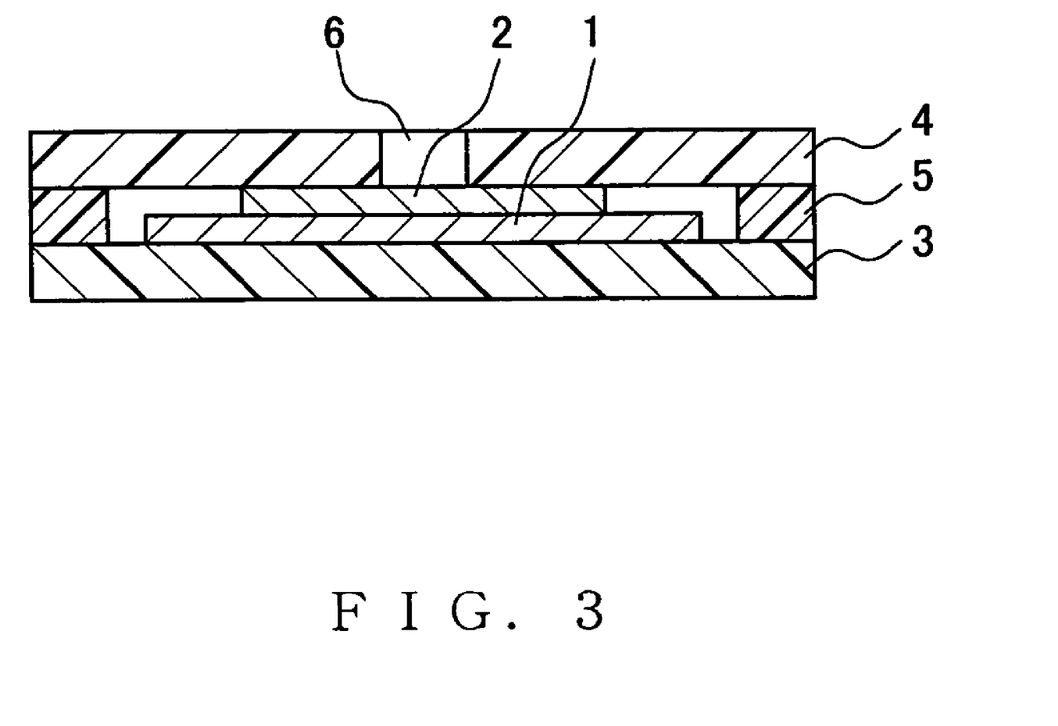
FIG. 3 is a cross-sectional view of the blood testing tool according to the example shown in FIGS. 2A and 2B.

A blood testing tool according to the present invention may include a holder, for example, and a laminate including a separation porous membrane and a recovery porous membrane may be contained in the holder. FIGS. 2A, 2B, and 3 show an example of a contained-type blood testing tool in which a laminate including a separation porous membrane 2 and a recovery porous membrane 1 is contained in a holder. FIG. 2A is a plan view of the contained-type blood testing tool as viewed from top, FIG. 2B is a back side view of the same, and FIG. 3 is a cross-sectional view taken in the arrow direction of line I—I in the plan view.

As shown in the drawings, in this blood testing tool, a spacer 5 is placed on the periphery of a square lower substrate 3, and on the spacer 5, a square upper substrate 4 is placed, thus forming a holder in which a laminate including the separation porous membrane 2 and the recovery porous membrane 1 is contained. Both the substrates 3 and 4 are transparent. A part of the periphery of each substrate is not provided with the spacer 5 so that a space is formed, which serves as an air vent portion 7. At the approximate center of the upper substrate 4, a hole 6 for supplying blood is formed. In the separation porous membrane 2 as the upper layer of the laminate, the portion at the approximate center and corresponding to the hole 6 is a blood supply portion.

In this blood testing tool, when blood is dropped on the blood supply portion of the separation porous membrane 2 through the hole 6, the blood moves in the thickness direction inside the separation porous membrane 2 by a capillary phenomenon. As the blood moves, blood cells are blocked inside the separation porous membrane 2 and thus only blood plasma or blood serum passes through the separation porous membrane 2. The blood serum or blood plasma having passed through the separation porous membrane 2 comes into contact with the recovery porous membrane 1 as the lower layer of the laminate and moves inside the recovery porous membrane 1 in the thickness direction and in the surface direction. Since this blood testing tool has the air vent 7, the blood moves quickly.

The size of the blood testing tool can be determined as appropriate according to, for example, the size of the laminate to be contained or the like. For example, the blood testing tool has an overall size of 5 mm×100 mm to 5 mm×100 mm and an overall thickness of 0.5 mm to 5 mm, the hole 6 has a diameter of 1 mm to 10 mm, and the space between the upper substrate 4 and the lower substrate 3 has a height of 0.1 mm to 2 mm. Preferably, the blood testing tool has an overall size of 10 mm×50 mm to 10 mm×50 mm and an overall thickness of 0.5 mm to 3 mm, the hole 6 has a diameter of 3 mm to 10 mm, and the space between the upper substrate 4 and the lower substrate 3 has a height of 0.1 mm to 1 mm. More preferably, the blood testing tool has an overall size of 10 mm×30 mm to 10 mm×30 mm and an overall thickness of 1 mm to 2 mm, the hole 6 has a diameter of 5 mm to 8 mm, and the space between the upper substrate 4 and the lower substrate 3 has a height of 0.3 mm to 1 mm. The size, thickness, and the like of the separation porous membrane and the recovery porous membrane are not particularly limited, and may be, for example, the same as those in the above-described embodiment, and a material for forming the holder may be the same as that for forming the supporter in the above-described embodiment.

In this blood testing tool, after blood has penetrated into the recovery porous membrane to develop and then been dried, the recovery porous membrane may be taken out, for example, by decomposing the blood testing tool and may be treated in the same manner as in the above-described embodiment.

EXAMPLES

Example 1 and Comparative Example 1

A contained-type blood testing tool as shown in FIGS. 2A, 2B, and 3 was produced, and the recovery rate of blood serum and the degree of hemolysis were measured.

(Recovery Porous Membrane)

A polyethersulfone asymmetric porous membrane (20 mm×20 mm, with a thickness of 320 μm) in which pores on the upper surface side have an average pore size of 100 μm and pores on the lower surface side have an average pore size of 5 μm was immersed in a 30 wt % sucrose aqueous solution, and then was dried.

(Production of Contained-type Blood Testing Tool)

To the periphery of a transparent PET lower substrate 3 (31 mm×31 mm, with a thickness of 188 μm) excluding the portion to be an air vent portion 7, a PET spacer 5 (with a width of 5 mm) was bonded using a double-faced tape. Then, the recovery porous membrane was disposed within the region surrounded by the spacer 5 on the lower substrate 3 in such a manner that the surface on the side with smaller pores faces the lower substrate 3. A polysulfone porous membrane (13 mm×13 mm, with a thickness of 320 μm) as a separation porous membrane further was laminated on the central portion of the recovery porous membrane in such a manner that the surface on the side with smaller pores faces the recovery porous membrane. In the separation porous membrane, pores on the upper surface side have an average pore size of 100 μm and pores on the lower surface side have an average pore size of 1 μm. Then, a transparent PET upper substrate 4 (31 mm×31 mm, with a thickness of 188 μm) having a hole 6 (with a diameter of 6 mm) at the approximate center thereof was bonded to the spacer 5 using a double-faced tape so that the laminate was enclosed.

(Method for Recovering Blood Serum)

100 μof whole blood of a healthy subject, which was collected using a heparin Na blood-collecting vessel, was dropped on the separation porous membrane 2 through the hole 6 of the blood testing tool. The blood serum was allowed to develop sufficiently in the recovery porous membrane 1, and this was then dried at room temperature for 24 hours. Subsequently, the recovery porous membrane 1 was taken out from the blood testing tool and was immersed in 200 μL of purified water. This was left at room temperature for 20 minutes and then subjected to centrifugation to collect a supernatant, which was used as a serum sample solution. In the same manner, 20 serum sample solutions in total were prepared from 20 specimens. Amounts of respective components and the degree of hemolysis in these samples were measured in the following manner. Furthermore, whole blood of the same healthy subject as in Example 1 was subjected to centrifugation (3000 rpm, 10 minutes), and blood plasma thus obtained was used as a control.

(Measurement of Amounts of Components)

Amounts of the respective components were measured with an autoanalyzer (product name "Hitachi 7070", manufactured by Hitachi, Ltd.), using the following commercially available kits (all manufactured by Roche Diagnostics K.K.) according to their application methods. In the respective measurements, purified water was used as a blank.

1. Glutamic—Oxaloacetic Transaminase (GOT)
    Product Name: LIQUI TECH GOT IFCC
2. Glutamic—Pyruvic Transaminase (GPT)
    Product Name: LIQUI TECH GPT IFCC
3. γ-Glutamyl Transpeptidase (γ-GTP)
    Product Name: LIQUI TECH γ-GTP IFCC 4. Creatinine
   Product Name: LIQUI TECH Creatinine PAP
5. Urea Nitrogen (BUN)
   Product Name: LIQUI TECH BUN
6. Glucose (Glc)
   Product Name: LIQUI TECH Glucose HK test
7. Triglyceride (TG)
   Product Name: LIQUI TECH TG
8. Total Cholesterol (T-Cho)
   Product Name: LIQUI TECH TC
9. High-Density Lipoprotein Cholesterol (HDL-C)
   Product Name: LIQUI TECH HDL-C
10. Uric Acid (UA)
    Product Name: LIQUI TECH UA Plus
11. Total Protein (TP)
    Product Name : RD Total Protein (Measurement of Degree of Hemolysis)

The degree of hemolysis was evaluated by measuring a hemoglobin concentration using a hemoglobin quantifying reagent, a product named "Hemo 2" manufactured by Intermedics Inc., according to its application method.

Figure 4:
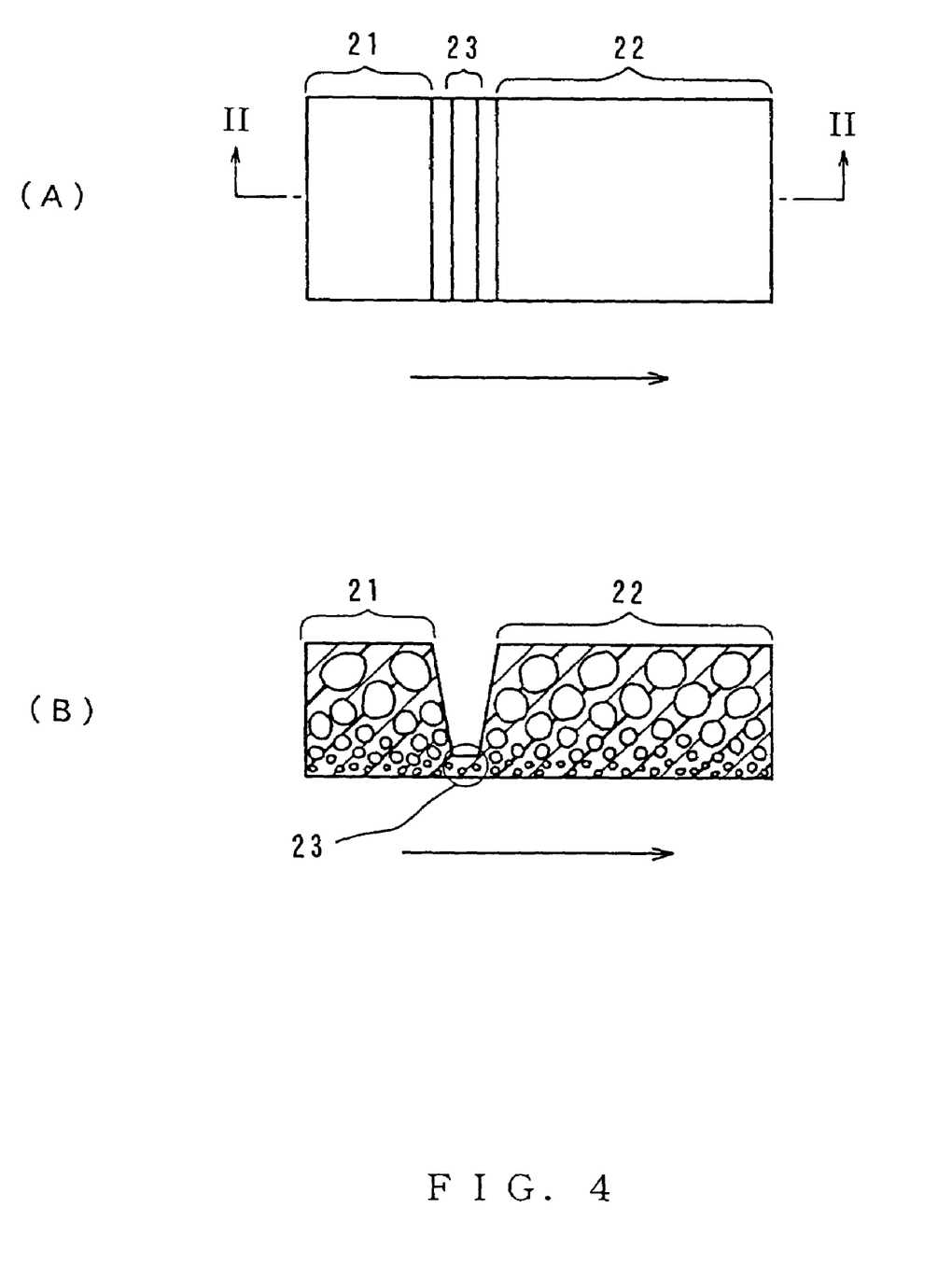
FIG. 4A is a plan view and FIG. 4B is a cross-sectional view.

Further, as Comparative Example 1, a blood testing tool as shown in FIGS. 4A and 4B employing transverse separation was produced in the following manner. FIG. 4A is a plan view of the blood testing tool and FIG. 4B is a cross-sectional view taken in the arrow direction of line II—II in the plan view. First, a strip-shaped asymmetric porous membrane (made of polysulfone, with a length of 35 mm, a width of 16 mm, a thickness of 330 µm, a maximum pore size of 100 to 500 µm, and a minimum pore size of 1 to 10 µm) was provided. The recovery porous membrane was immersed in the above-described sucrose solution and then dried in the same manner as in Example 1. At a location 11 mm along the length of the porous membrane with respect to one of its ends, a disc roller was pressed against and rolled on the portion to form a groove (with a minimum width of 0.8 mm, a maximum width of 1.2 mm, and a depth of 180 to 220 µm) in its width direction, thus producing a blood testing tool as shown in FIGS. 4A and 4B. In these drawings, the portion to the left of the groove is a blood supply portion 21, the portion to the right of the groove is a development portion 22, and the portion between the bottom of the groove and the part of the surface of the asymmetric porous membrane corresponding to the bottom is a blood-cell blocking portion 23. In this blood testing tool, the blood supply portion 21 has a length of 11 mm and the development portion 22 has a length of 23 mm.

100µl of whole blood of the same healthy subject as in Example 1 was dropped on the center portion of the blood supply portion. In this blood testing tool, when blood is dropped on the surface (the upper surface in FIG. 4B) of the blood supply portion 21 with larger pores, the blood moves in the thickness direction inside the blood supply portion 21 while separating blood cells and also moves in the surface direction (the direction indicated with an arrow in FIG. 4B). In the blood that has moved in the surface direction to reach the blood-cell blocking portion 23, blood cells cannot pass through the blood-cell blocking portion 23 and are captured. As a result, only blood plasma or blood serum having passed through the blood-cell blocking portion 23 develops in the development portion 22.

The blood serum obtained by separating the blood cells in the blood-cell blocking portion 23 was allowed to develop sufficiently in the development portion 22, which then was dried. Subsequently, the development portion 22 was cut out from the blood testing tool and further was cut to be in a strip shape. This cut piece was immersed in 200 µL of purified water. This was left at room temperature for 20 minutes and then subjected to centrifugation to collect a supernatant, which was used as a serum sample solution. Then, in the same manner as described above, 20 serum sample solutions in total were prepared from 20 specimens. Amounts of respective components and the degree of hemolysis in these samples were measured in the same manner as in Example 1.

Table 1 below shows the results of the measurements, in which the measured values of Example 1 and Comparative Example 1 are indicated as relative values (percentages on average) with respect to the measured values of the control as 100%.

TABLE 1

|  | Example 1 (%) | Comparative Example 1 (%) |
| --- | --- | --- |
| GOT | 17 | 10 |
| GPT | 16 | 10 |
| γ-GTP | 11 | 6 |
| Creatinine | 22 | 12 |
| BUN | 13 | 12 |
| Glc | 15 | 12 |
| TG | 15 | 10 |
| T-Cho | 13 | 9 |
| HDL-C | 12 | 8 |
| UA | 15 | 10 |
| TP | 12 | 9 |
| Degree of hemolysis | 4.6 | 6.8 |

As shown in Table 1, the serum samples prepared using the blood testing tool of the present invention exhibited higher relative values with respect to the control than the serum samples prepared using the blood testing tool employing transverse separation according to the comparative example. Thus, it is understood that the blood testing tool of the present invention can recover blood serum with a high recovery rate. Besides, the degree of hemolysis in the serum samples prepared using the blood testing tool of the present invention was lower than that in the serum samples prepared using the blood testing tool of the comparative example. Thus, it is understood that the blood testing tool of the present invention can prevent the hemolysis as seen in a conventional laminate-type blood testing tool.

Example 2, Comparative Example 2, and Comparative Example 3

As Example 2, a contained-type blood testing tool as shown in FIGS. 2A, 2B, and 3 was produced, and the degree of hemolysis was measured in the same manner as in Example 1.

On the other hand, as Comparative Example 2, a contained-type blood testing tool was produced in the same manner as in Example 1 except that filter paper (product name "BFC 180", manufactured by Whatman plc.) with a length of 20 mm, a width of 20 mm, and a thickness of 450 µm was used in place of the recovery porous membrane. The degree of hemolysis also was measured in the same manner as in Example 1. The filter paper has an average pore size of 1 to 5 µm.

Furthermore, as Comparative Example 3, a blood testing tool in which pores on the upper surface side of a recovery porous membrane have an average pore size that is smaller than that of pores on the lower surface side of a separation porous membrane was used. The blood testing tool of Comparative Example 3 was a contained-type blood testing tool produced in the same manner as in Example 1 except that the same asymmetric porous membrane as the recovery porous membrane used in Example 1 was disposed within the region surrounded by the spacer on the transparent PET lower substrate in such a manner that the surface on the side with larger pores faces the lower substrate as opposed to Example 1. The contained-type blood testing tool of Comparative Example 3 has the same size as that of the contained-type blood testing tool of Comparative Example 2 except that the recovery porous membrane has a pore size distribution in which an average pore size varies so that it is increased continuously in the thickness direction.

Blood was supplied to the contained-type blood testing tools of Comparative Examples 2 and 3, and blood serum was recovered and subjected to the measurement of the degree of hemolysis in the same manner as in Example 2. This series of operation was repeated 10 times (n=10) in total. The average values determined are shown in Table 2 below along with the standard deviations (SD).

TABLE 2

|  | Degree of Hemolysis (mg/100 mL) | SD (n = 10) |
|---|---|---|
| Example 2 | 4.60 | 2 |
| Comparative Example 2 | 36.6 | 9 |
| Comparative Example 3 | 306.2 | 60 |

As shown in Table 2, it was confirmed that hemolysis occurred in the blood testing tool of Comparative Example 2 in which an average pore size of the pores on the upper surface side of the recovery porous membrane is equal to or smaller than that of the pores on the lower surface side of the separation porous membrane. Especially in the blood testing tool of Comparative Example 3, the degree of hemolysis was considerable. In contrast, the blood testing tool according to the present invention could sufficiently reduce the occurrence of the hemolysis.

INDUSTRIAL APPLICABILITY

As specifically described above, according to the blood testing tool of the present invention, blood plasma or blood serum can be recovered with a high yield and blood cells can be separated adequately without causing hemolysis. Thus, even with a small amount of blood sample, an effective test can be conducted. Therefore, the blood testing tool of the present invention is useful, for example, in fields such as clinical medicine, particularly in a remote clinical testing system in which the amount of collected blood is limited.

The invention claimed is:

1. A blood testing tool comprising:
    an asymmetric separation porous membrane for separating blood cells from blood; and
    an asymmetric recovery porous membrane to be impregnated with and retain blood serum or blood plasma of the blood such that an upper surface side of the recovery porous membrane is underneath a lower surface side of the separation porous membrane, the separation porous membrane being laminated on the recovery porous membrane,
    wherein pores on the upper surface side of the recovery porous membrane have an avenge pore size that is in a range from 10 to 1000 μm and is larger than that of pores on the lower surface side of the separation porous membrane, and further
    wherein the pores on the lower surface side of the separation porous membrane have an average pore size that does not allow the blood cells to pass.

2. The blood testing tool according to claim 1, wherein the pores on the upper surface side of the recovery porous membrane have an average pore size that is 10 to 100 times larger than that of the pores on the lower surface side of the separation porous membrane.

3. The blood resting tool according to claim 1, wherein the pores on the lower surface side of the separation porous membrane have an average pore size in a range from 1.0 to 10 μm.

4. The blood testing tool according to claim 1, wherein the separation porous membrane is an asymmetric porous membrane with a pore size distribution in which an average pore size varies so that it is reduced continuously or discontinuously in a thickness direction.

5. The blood testing tool according to claim 1, wherein the recovery porous membrane is an asymmetric porous membrane with a pore size distribution in which an average pore size varies so that it is reduced continuously or discontinuously in a thickness direction.

6. The blood testing tool according to claim 1, wherein the recovery porous membrane is supported by a supporter.

7. The blood testing tool according to claim 1, wherein the porous membranes are formed using at least one resin selected from the group consisting of polysulfone, polyamide, polyimide, polycarbonate, polystyrene, and polyaryl hydrazide.

8. The blood testing tool according to claim 1, wherein the porous membranes are treated to be provided with hydrophilicity.

9. The blood testing tool according to claim 1, wherein the porous membranes are configured as removable laminations such that the recovery porous membrane remains unbroken upon separation of the porous membranes.

* * * * *